US007154010B2

United States Patent
Kumbhar et al.

(10) Patent No.: US 7,154,010 B2
(45) Date of Patent: Dec. 26, 2006

(54) INTEGRATED PROCESS FOR THE PRODUCTION OF BISPHENOL A FROM CUMENE HYDROPEROXIDE

(75) Inventors: Pramod Shankar Kumbhar, Bangalore (IN); Jegadeesh Thampi, Bangalore (IN); Bharat Singh, Bangalore (IN); John W. Fulmer, Mt. Vernon, IN (US); Prashant Anil Tatake, Bangalore (IN)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 10/250,107

(22) Filed: Jun. 4, 2003

(65) Prior Publication Data

US 2004/0249223 A1     Dec. 9, 2004

(51) Int. Cl.
*C07C 36/16*       (2006.01)
(52) U.S. Cl. ...................... 568/728; 568/798
(58) Field of Classification Search ................ 568/728, 568/798
See application file for complete search history.

(56) References Cited

U.S. PATENT DOCUMENTS

| | | | |
|---|---|---|---|
| 2,468,982 A | 5/1949 | Jansen | |
| 2,923,744 A | 2/1960 | Scriabine et al. | |
| 3,172,916 A | 3/1965 | Wagner | |
| 3,394,089 A | 7/1968 | McNutt et al. | |
| 4,294,995 A | 10/1981 | Faler et al. | |
| 4,369,293 A | 1/1983 | Heydenreich et al. | |
| 4,387,251 A | 6/1983 | Meyer et al. | |
| 4,396,728 A | 8/1983 | Faler | |
| 4,423,252 A | 12/1983 | Maki et al. | |
| 4,455,409 A | 6/1984 | Faler et al. | |
| 4,490,565 A | 12/1984 | Chang et al. | |
| 4,490,566 A | 12/1984 | Chang et al. | |
| 4,870,217 A | 9/1989 | Knifton | |
| 4,898,987 A | 2/1990 | Knifton | |
| 4,898,995 A | 2/1990 | Knifton et al. | |
| 4,931,594 A | 6/1990 | Knebel et al. | |
| 4,996,373 A | 2/1991 | Bottenbruch et al. | |
| 5,113,034 A | 5/1992 | Soled et al. | |
| 5,212,206 A | 5/1993 | Rudolph et al. | |
| 5,302,774 A | 4/1994 | Berg et al. | |
| 5,315,042 A | 5/1994 | Cipullo et al. | |
| 5,777,180 A * | 7/1998 | June et al. .................. | 568/728 |
| 5,824,622 A | 10/1998 | Harmer et al. | |
| 5,939,494 A | 8/1999 | Wehmeyer et al. | |
| 6,013,845 A * | 1/2000 | Allan et al. .................. | 568/728 |
| 6,169,215 B1 | 1/2001 | Levin et al. | |
| 6,169,216 B1 | 1/2001 | Levin et al. | |
| 6,297,406 B1 | 10/2001 | Levin et al. | |

OTHER PUBLICATIONS

Arata et al., Synthesis of solid superacid of tungsten oxide supported on zirconia and its catalytic action, Proceedings of 9th International Congress on Catalysis, pp. 1727-1735, vol. 4, 1988.
Hino et al., Reactions of Butane and Isobutane Catalysed by Titanium Oxide treated with Sulphate Ion. Solid Superacid Catalyst, J.C.S. Chem. Comm., p. 1148, 1979.
Kumbhar et al., Chemically Modified Oxide Surfaces, Chemically Modified Surfaces, pp. 81-92, vol. 3, 1989.
Singh, Preparation of bisphenol-A over zeolite catalysts, Catalysis Letters, , pp. 431-435, vol. 16, 1992.
Das et al, Sulfonic acid Functionalized mesoporous MCM-41 silica as a convenient catalyst for Bisphenol-A synthesis, Chem.Communication, Aug. 7, 2001, pp. 2178-2179.

* cited by examiner

*Primary Examiner*—Samuel Barts
(74) *Attorney, Agent, or Firm*—Marina Larson & Associates, LLC

(57) ABSTRACT

Use of a specific combination of catalysts for the first and second steps of the process for the conversion of CHP to BPA provides high yields of BPA and low impurity yields, without a requirement for the intermediate purification steps. In the first step, CHP is cleaved in the presence of a sulfated metal oxide catalyst such as sulfated Zirconia to produce phenol and acetone. In the second step, the phenol and acetone produced is reacted, preferably without intermediate purification, in the presence of a cation exchange resin catalyst that includes a cation exchange resin and a mercaptan or mercaptoalkanoic acid promoter to produce BPA.

34 Claims, 3 Drawing Sheets

INTEGRATED PROCESS FOR THE PRODUCTION OF BISPHENOL A FROM CUMENE HYDROPEROXIDE

BACKGROUND OF INVENTION

This application relates to an integrated process for the production of bisphenol A (BPA) from cumene hydroperoxide (CHP).

Bisphenol A is an important reactant used in the production of polycarbonate resins. A known method for the production of BPA involves the catalytic breakdown of CHP to phenol and acetone, and the subsequent reaction of the phenol and acetone in the presence of an acidic catalyst to form BPA. Various catalysts are known for use in each of these two steps.

Cleavage of CHP with homogeneous catalysts such as sulphuric acid is widely practiced. Heterogeneous cleavage of CHP over various solid acid catalysts has also been reported. For example, U.S. Pat. No. 5,824,622 discloses porous microcomposites of perfluorinated ion-exchange polymers and metal oxides, networks of silica, and networks of metal oxide and silica as catalysts and indicates that they can be used as catalysts, for example, for alkylating aliphatic or aromatic hydrocarbons, for decomposing organic hydroperoxides, such as CHP, for sulfonating or nitrating organic compounds, and for oxyalkylating hydroxylic compounds. PCT Publication WO 03/002499 refers to similar catalysts and demonstrates the not surprising result that reducing the particle size of the catalyst (and therefore increasing the catalytic surface area) enhances the reaction rates in decomposition of CHP and suggests the use of the same catalyst for both CHP decomposition and BPA synthesis. Other catalysts that can be used in the cleavage of CHP include solid acid catalysts such as zeolite beta, disclosed in U.S. Pat. No. 4,490,565; a Constraint index 1–12 zeolite, such as ZSM-5, disclosed in U.S. Pat. No. 4,490,566; faujasite, disclosed in EP-A-492807; smectite clays, described in U.S. Pat. No. 4,870,217; ion exchange resins having sulfonic acid functionality or heteropoly acids, such as 12-tungstophosphoric acid, on an inert support, such as silica, alumina, titania and zirconia, disclosed in U.S. Pat. No. 4,898,995. Additional solid-acid catalysts suited for use in the present invention include those comprising a sulfated transition metal oxide such as sulfated zirconia together with an oxide of iron or oxides of iron and manganese as described in U.S. Pat. No. 6,169,216, as well as those comprising a mixed oxide of cerium and a Group IVB metal, e.g., zirconium, described in U.S. Pat. No. 6,297,406. Other known solid acid catalysts comprise an oxide of a Group IVB metal modified with an oxyanion or oxide of a Group VIB metal by calcination of the oxide species at a temperature of at least 400.degree. C., as disclosed in U.S. Pat. No. 6,169,215. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; and in an article by K. Arata and M. Hino in Proceedings of 9th International Congress on Catalysis, Volume 4, pages 1727–1735 (1988). The macroreticular acid ion exchange resin used is typified by the presence of sulfonic acid groups, e.g., the sulfonated styrene-divinylbenzene copolymer exchange resins such as those commercially available as Amberlyst-15, Amberlyst XN-1005, Amberlyst XN-1010, Amberlyst XN-1011, Amberlyst XN-1008 and Amberlite 200.

For catalyzing the formation of BPA from phenol and acetone, numerous sources disclose the use of cation exchange resin catalysts. For example, U.S. Pat. No. 5,315,042 discloses ion exchange resin catalysts such as sulfonated polystyrene or sulfonated poly(styrenedivinylbenzene) resins for this purpose. The use of divalent sulphur compounds such as mercaptans and glycolic acids to increase the reaction rate is also indicated. Sulphonated polystyrene-divinylbenzene ion-exchange resins with a portion of the sulphonic acid groups converted into mercaptan functionality were found better catalysts than unmodified resin (U.S. Pat. No. 3,172,916, U.S. Pat. No. 3,394,089). The use of zeolites coated with mercaptoamine at 120–180° C. has been reported (JP7420565). Singh (Catal. Lett., 27 (1992) 431) has discussed in detail the synthesis of BPA over zeolite catalysts such as H-ZSM-5, H-mordenite, H-Y and RE-Y vis-a-vis Amberlyst-15 and shown that zeolites with larger openings are more selective for this process although ion exchange resins are more active than zeolites. However, the general trend shows that modified ion exchange resins are the catalysts used worldwide for an optimum yield of bisphenol-A. Alkylation of propenyl halide with phenol using Friedel Crafts catalysts for the synthesis of BPA has been reported, (Fr. Demande 2,646,418, 1990). Conversions to the extent of 60% are obtained in the above mentioned process. Some monographs mention the use of commercial acid treated clays for the synthesis of bisphenol-A (Preparative Chemistry using Supported Reagents, Academic Press, San Diego, Calif., 1987, Solid Supports and Catalysts in Organic Synthesis, Ellis Horwood, Chechester, U.K., 1992). Scriabine et al. (U.S. Pat. No. 2,923,744) produce Bisphenol A using sulfuric acid, promoted by mercaptoalkanesulfonic acids or salts or corresponding sulfonate esters at a level of 0.1–5% by weight of the base charge, to catalyze condensation of acetone and phenols, when used in amounts of 0.1 to 5% by weight based on total charge. Sulfuric acid is used in amounts of about 2 moles per mole of acetone. The reactions can be run in halogenated hydrocarbon solvents. Bottenbruch et al. (U.S. Pat. No. 4,996,373) have proposed a process for producing dihydroxyaryl compounds from carbonyl compounds and phenols under high pressure, in the presence of various catalysts, including sulfonic acid resins. Catalysts containing thiol functionality, e.g. ion exchange resins treated with mercapto compounds, have been disclosed for this use. Meyer et al. (U.S. Pat. No. 4,387,251) have proposed processes for making 4,4'-dihydroxydiphenyl alkanes using aromatic sulfonic acids as condensing agents. Jansen (U.S. Pat. No. 2,468,982) has proposed preparation of bisphenols using anhydrous hydrogen chloride in combination with a mercaptoalkanoic acid, which may be formed in situ by reaction of a mercaptol with the ketone, as condensing agent. Knebel et al. (U.S. Pat. No. 4,931,594) disclose the use of large amounts of sulfonic acid resin, mixed with uncombined 3-mercaptopropionic acid, to cause the condensation to occur. It has been proposed in British Patent 1,185,223 to use a mixture of insoluble resins, one a sulfonic acid resin and the other a resin containing mercapto groups, for making bisphenols. Randolph et al. (U.S. Pat. No. 5,212,206) disclose a catalyst, made by treating a sulfonated ion-exchange resin with a dialkylaminomercaptan. Other references, representative of references on modification of sulfonic acid ion-exchange resins, include Wagner (U.S. Pat. No. 3,172,916). McNutt et al. (U.S. Pat. No. 3,394,089), Faler et al. (U.S. Pat. Nos. 4,455,409; 4,294,995 and 4,396,728); Heydenrich et al. (U.S. Pat. No. 4,369,293); Berg et al. (U.S. Pat. No. 5,302,774) and Maki et al. (U.S. Pat. No. 4,423,252). The reactive catalysts generally include mercapto-functions attached to a sulfonic acid group in the form of a sulfonamido or ammonium sulfonate salt.

SUMMARY OF INVENTION

The present invention provides a specific combination of catalysts for the first and second steps of the process for the conversion of CHP to BPA that provides high yields of BPA and low impurity yields, without a requirement for intermediate purification steps. In accordance with the method of the invention, BPA is produced from CHP by a method comprising the steps of:
  (a) cleaving CHP in the presence of a solid sulfated metal oxide catalyst to produce phenol and acetone; and
  (b) reacting the phenol and acetone produced in step (a), preferably without intermediate purification, in the presence of a cation exchange resin catalyst to produce BPA.

DETAILED DESCRIPTION

Figure 1:
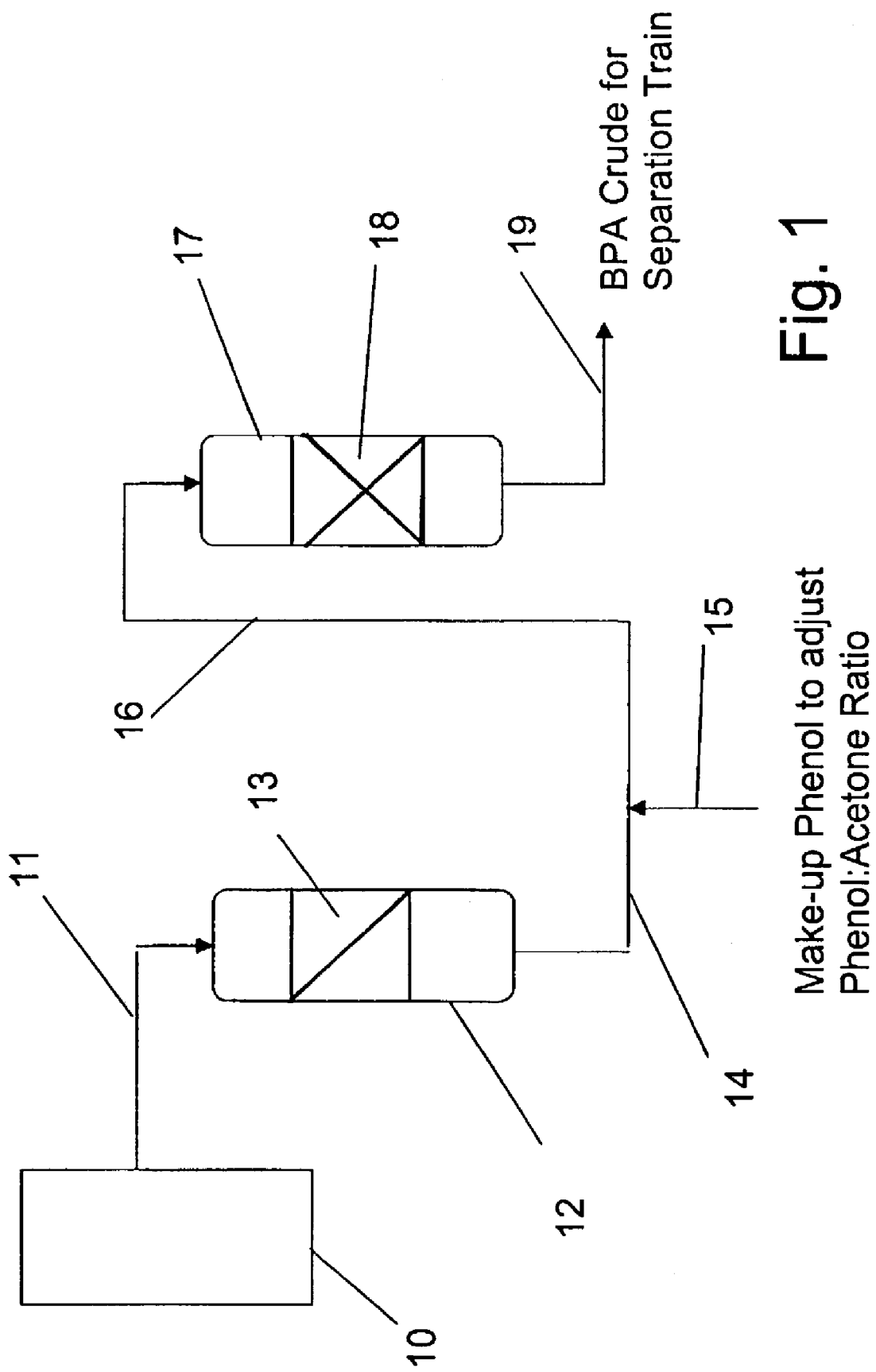
FIG. 1 shows a schematic representation of a first embodiment of a facility for making BPA in accordance with the invention.

In the specification and claims of this application, numerical values are expressed as integer values. It will be appreciated that values that when expressed to the same number of significant digits as these integer values are equal to the integer values.

The present invention provides a method for production of BPA starting from CHP. Unlike prior methods, the combination of catalysts employed in the present invention allows the synthesis of BPA directly from the CHP cleavage mass without requiring time consuming and expensive intermediate purification steps. In addition, the ratio of para,para-bisphenol (p-p) to ortho,para-bisphenol (o-p) in the product highly favors the desired p-p product, with selectivity in excess of 90%.

The first step in the method of the invention is cleaving CHP in the presence of a solid sulfated metal oxide acid catalyst like sulfated Zirconia to produce a cleavage mass comprising phenol and acetone. This cleavage mass is substantially free of hydroxy acetone. The sulfated metal oxide catalyst is a metal hydroxide or metal oxide, hydroxide or oxide of the metals chosen from a group formed from group metals belonging to group IV of periodic table such as titanium, zirconium, hafnium, germanium, tin, lead, and aluminium or iron sulfated with a source of sulfate ion, such as sulfuric acid or more preferably, ammonium sulfate. Solid acid catalyst thus obtained has acid strength, in terms of Hammett acidity equation, of Ho<−12 and sulfur content of 0.5~10 weight %. Therefore, as regards the solid acid catalyst being used in the present invention is desired to have acid strength, in terms of Hammett acidity equation, of Ho<−12 and sulfur content of 0.5~10 weight %, desirably, 0.5~5 weight %. Sulfated metal oxide catalysts can be prepared by calcination of the metal hydroxide in the presence of sulfate ions. (Hino and Arata, JCS Chemical Communications, p. 1148, 1979; Kumbhar et al. in "Chemically Modified Oxide Surfaces", Ed. D. E. Leyden, Gordon and Breech, p. 81, 1989).

CHP obtained from the oxidation of cumene (technical CHP) generally comprises around 80% CHP, the remainder being Dimethyl benzylalcohol (DMBA), α-Methyl styrene (AMS), cumene and acetophenone. This material or a CHP composition of comparable or higher purity is added, along with 10 to 100% by weight acetone relative to the amount of CHP to a reactor containing the solid acid catalyst such as sulfated Zirconia or other metal oxide. The reactor may be a batch, semi-continuous or continuous reactor. Suitable catalyst loading levels are 2 to 8% by weight based on the total weight of the feed, for example 5%. The temperature is maintained in the range of 45 to 85° C., preferably 55 to 65° C. The reaction is allowed to proceed for a period of time sufficient to substantially convert CHP to phenol and acetone. As will be apparent to persons skilled in the art, the specific time period will depend on the volume and catalytic surface area in the reactor, the temperature and other apparatus specific parameters. Similarly, in a continuous process, it will be appreciated that the reaction time is determined by the reactor volume and flow rate. As used in this application, the term "substantially convert" means conversions of at least 90%, preferably at least 95% of the CHP to phenol and acetone.

The second step in the method of the invention is reacting the phenol and acetone produced from the cleavage of the CHP in the presence of a cation exchange resin catalyst to produce bisphenol A. The cation exchange resin catalyst comprises a cation exchange resin and a mercaptan rate accelerator or a mercaptoalkanoic acid as a bulk promoter.

Suitable cation exchange resins include, without limitation, sulfonated styrenedivinylbenzene copolymer exchange resins such as those commercially available as Amberlyst-15, Amberlyst XN-1005, Amberlyst XN-1010, Amberlyst XN-1011, Amberlyst XN-1008 and Amberlite 200. Preferably the cation exchange resin is cross-linked, for example 1 to 25% cross-linked. The specific cation exchange resin used in the example below is a microreticular gel type resin, Amberlyst XE-760(XE-760) (Rohm & Haas).

The mercaptan portion of the cation exchange resin catalyst is suitably pyridyl ethyl Mercaptan (PEM) or other mercaptan promoters as described in commonly assigned U.S. Pat. No. 6,534,686 which is incorporated herein by reference. The mercaptan is loaded on the catalyst in loading of from 20 to 70% by weight, preferably 35 to 60%, more preferably 40 to 55%.

In the second step, the composition of the cleavage mass is suitably adjusted so that acetone and phenol are present in a mole ratio of 1:35 to 1:10, more preferably 1:20 to 1:10, and most preferably 1:13. The cleavage mass is introduced to a second reactor containing the cation exchange resin catalyst. This may be a batch, semi-continuous or continuous reactor. The second reactor is suitably maintained at a temperature of 40 to 100° C., more preferably 60 to 85° C., most preferably 75° C. for a period of time sufficient to substantially convert the acetone, the limiting reactant in the cleavage mass, to bisphenol A. As will be apparent to persons skilled in the art, the specific time period will depend on the volume and catalytic surface area in the reactor, the temperature and other apparatus specific parameters. As used in this application, the term "substantially convert" means conversions of at least 90%, preferably at least 95% of the acetone to BPA. The catalyst loading in the second step of the process is suitably 1 to 10% by weight of the total feed, preferably 3 to 7%, most preferably about 5%.

Figure 2:
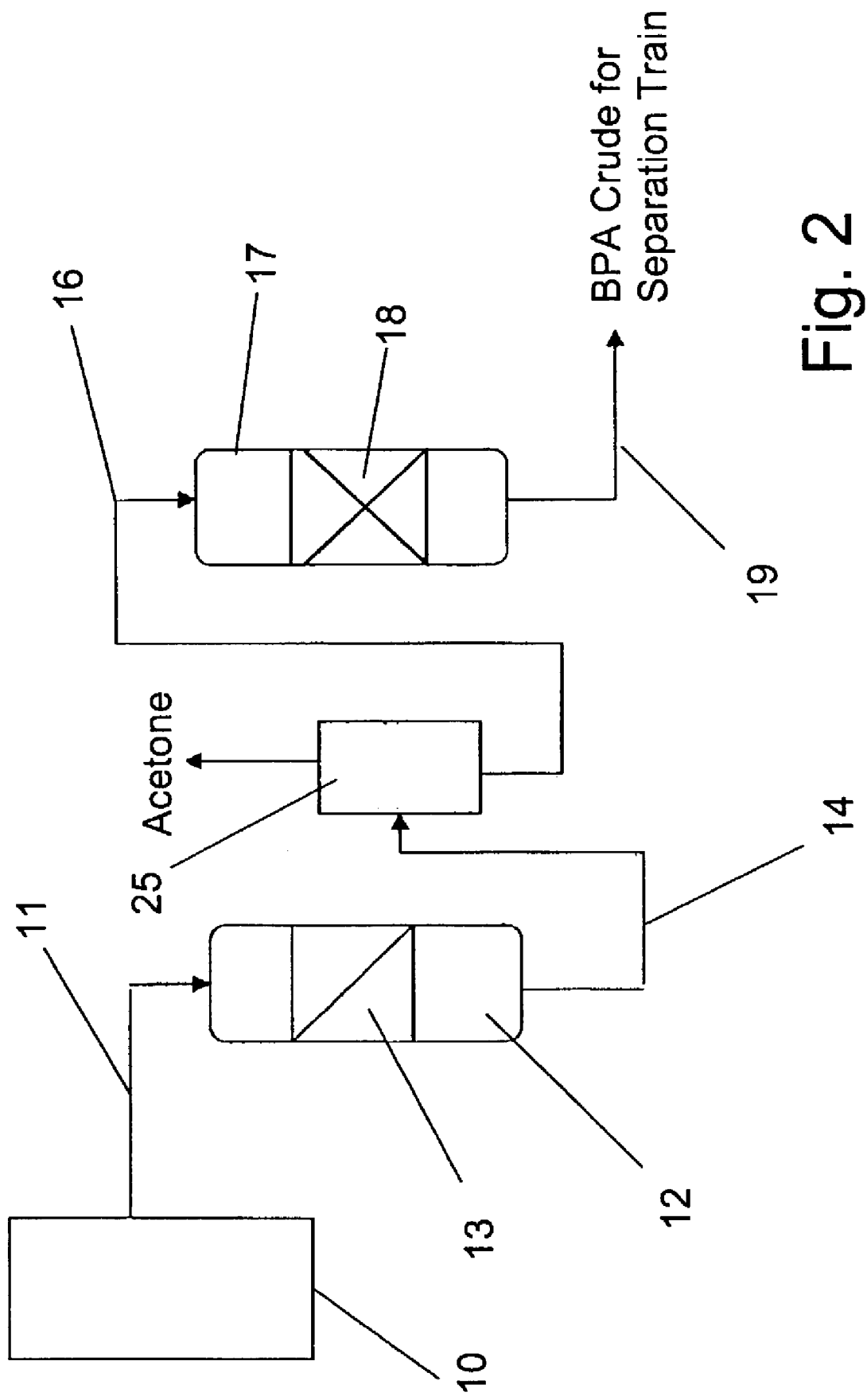
FIG. 2 shows a schematic representation of a second embodiment of a facility for making BPA in accordance with the invention.

The method of the invention can be suitably practiced in a plant or facility in accordance with the invention. FIGS. 1 and 2 show schematic representations of two alternative embodiments of such a facility. As shown in FIGS. 1 and 2, a reservoir 10 containing CHP and acetone is connected via line 11 to a reactor 12. The reactor 12 contains a catalyst bed 13 comprising a solid acid catalyst such as sulfated Zirconia. The product from reactor 12 is recovered via line 14 and passed through a system for adjusting the acetone:phenol mole ratio to a desired level. In FIG. 1, this system is makeup line 15 which supplies additional phenol. In FIG. 2, this system is a flash distillation column 25 which removes acetone from the cleavage mass produced in reactor 12 to achieve the desired acetone:phenol mole ratio. After passing through the system for adjusting the acetone:phenol mole ratio, the cleavage mass is transported via line 16 to a second reactor 17 containing a cation exchange resin catalyst 18. Crude BPA is recovered from the second reactor 17 via line 19, and may be further purified if desired.

Figure 3:
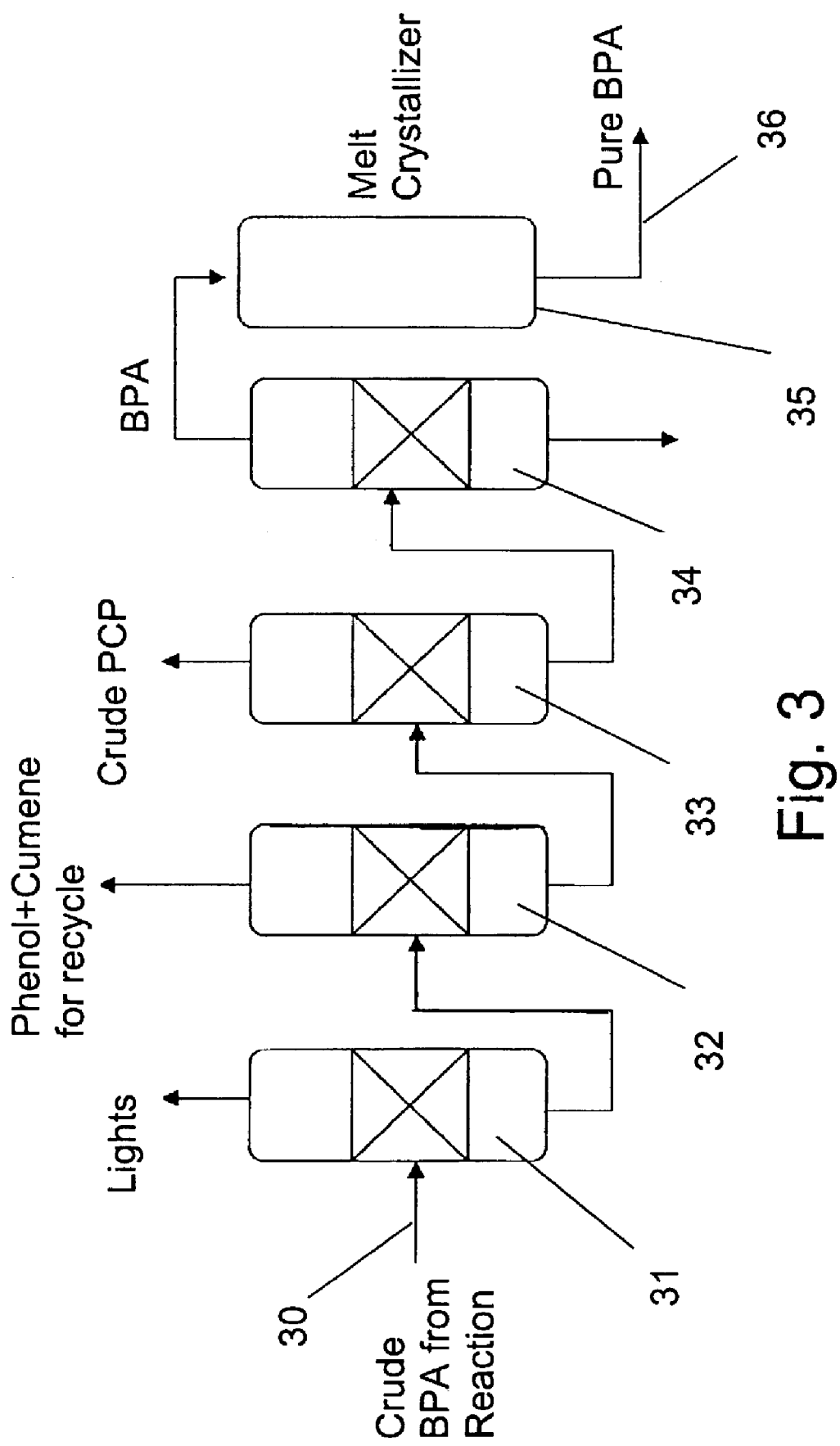
FIG. 3 shows a schematic representation of a separation section for purifying BPA produced using the method of the invention.

FIG. 3 shows a separation section suitable for further purification of the crude BPA. As shown, the crude BPA stream 30 is fed through successive distillation columns 31, 32, 33 and 34. In the first column 31, highly volatile impurities such as mesityl oxide, aldehydes, acetone etc. are removed. In the second column 32, phenol and cumene are recovered and can be recycled as desired. In the third column 33, crude p-cumyl phenol (PCP), dimers of Alpha-methyl styrene are removed. In the final column 34, the distilled fraction is BPA The distilled BPA is the fed to a melt crystallizer 35 from which pure BPA is recovered via line 36.

The invention will now be further described with reference to the following, non-limiting examples.

EXAMPLE 1

Commercially available Sulfated Zirconia (MEL Chemicals—X20 999/01:S019270, Engelhard—ZrO530E1/16) calcined at 600° C. in flowing air for three hours was used as a catalyst.

25.3 g technical 80% CHP (analyzed as 81% CHP, 8.7% DMBA, 1.36% alpha-methyl styrene, 0.7% Acetophenone and 7.2% Cumene) was added slowly to a mixture of 16.33 ml acetone and 1.658 g sulfated zirconia at 55° C. The addition was controlled to maintain the reaction temperature at no higher than 65° C. After the completion of the addition of CHP, the mixture was agitated for another half hour at 55° C. and analyzed using gas chromatography for completion. Phenol was obtained in a yield of 98% based on CHP.

5 g of the above-reaction mixture was added to a mixture of 55.188 gm phenol to adjust the acetone to phenol molar ratio of the mixture to 1:13, and 3 g 40% PEM on XE-760 cation exchange resin at 75° C. The reaction mixture was maintained at this temperature for 12 hrs and analyzed by GC. The yield of p,p-BPA was 94% based on CHP, with a p-p to o-p ratio of 97%.

EXAMPLE 2

A mixture of CHP (analyzed as 81 wt. % CHP, 8.7% DMBA, 1.36% AMS, 0.7% Acetophenone and 7.2% Cumene) and acetone (CHP:acetone volume ratio 1.5:1) was introduced through an inlet at a point above catalyst bed under CHP decomposition conditions including a temperature of about 50 to 90° C., a pressure of 0 to 10 psig, and a WHSV of 0.1 to 2 hr$^{-1}$ to provide a product comprising phenol and acetone. The catalyst bed is a packed bed of sulfated Zirconia catalyst. The catalyst is in the form of particles, typically, in the size range of 400 to 600µ, such that the catalyst bed void volume allows for liquid flow down the bed. Phenol was obtained in a yield of greater than 95% based on CHP for more than 24 hours on stream.

5 g of the above-reaction mixture was added to mixture of 55.188 gm phenol to adjust the mixture to an acetone to phenol molar ratio of 1:13, and 3 g 40% PEM on XE-760 cation exchange resin at 75° C. The reaction mixture was maintained at this temperature for 12 hrs and analyzed by GC. The yield of p,p-BPA was 92.1% based on CHP, with a p-p to o-p ratio of 96%.

EXAMPLE 3

The method of example 1 was repeated at the same operating conditions, but this time 0.602 g 3-mercaptopropionic acid (3-mpa) was used as a bulk promoter along with 3 g XE-760 as catalyst for the BPA synthesis. The molar yield of p,p-BPA obtained was 89.2% (based on CHP) and the p-p to o-p ratio of BPA was 95%.

COMPARATIVE EXAMPLE 1

The experiment of Example 1 was performed, except that 2 g XE-760 (Rohm and Haas) was used in place of sulfated zirconia as the CHP cleavage catalyst and in the second step of BPA synthesis 3 gm XE 760 was used in place of 40% PEM on XE-760 as the catalyst. The molar yield of p,p-BPA obtained was 50.9% (based on CHP) with a p-p to o-p ratio of 88.97%.

COMPARATIVE EXAMPLE 2

The experiment of example 1 was performed, except that sulfuric acid (300 ppm) was used in place of sulfated zirconia as the CHP cleavage catalyst. Comparable selectivity was obtained, but the yield of p,p-BPA was only 18.45% based on CHP.

COMPARATIVE EXAMPLE 3

The method of example 1 was repeated at the same operating conditions, but this time the catalyst used for the CHP cleavage was 2.0 g Amberlyst XE-760 (Rohm & Hass). Phenol yield was 95% while the molar yield of p,p-BPA obtained was 85.4% (based on CHP) and the p-p to o-p ratio of BPA was 97.3%.

The invention claimed is:

1. A method for production of bisphenol A comprising the steps of:
   (a) cleaving cumene hydroperoxide in the presence of a sulfated metal oxide acid catalyst to substantially convert the cumene hydroperoxide to a cleavage mass comprising phenol and acetone; and
   (b) reacting the cleavage mass in the presence of a cation exchange resin catalyst comprising a cation exchange resin and a mercaptan or mercaptoalkanoic acid promoter to substantially convert the phenol and acetone in the cleavage mass to bisphenol A.

2. The method of claim 1, wherein the cleavage mass produced in step (a) is reacted in step (b) without intermediate purification.

3. The method of claim 2, wherein the step of cleaving the cumene hydroperoxide is performed at a temperature of 55 to 65° C.

4. The method of claim 3, further comprising the step of adding phenol to or removing acetone from the cleavage mass formed in step (a) to attain an acetone:phenol mole ratio of 1:20 to 1:10.

5. The method of claim 4, wherein the acetone:phenol mole ratio attained is 1:13.

6. The method according to claim 3, wherein step (b) is performed at a temperature of 40 to 100° C.

7. The method of claim 6, further comprising the step of adding phenol to or removing acetone from the cleavage mass formed in step (a) to attain an acetone:phenol mole ratio of 1:20 to 1:10.

8. The method of claim 7, wherein the acetone:phenol mole ratio attained is 1:13.

9. The method of claim 2, wherein the cation exchange resin catalyst comprises pyridyl ethyl mercaptan as promoter.

10. The method of claim 9, wherein the pyridyl ethyl mercaptan is loaded on the cation exchange resin in an amount of 20 to 70% by weight.

11. The method of claim 10, wherein the pyridyl ethyl mercaptan is loaded on the cation exchange resin in an amount of 40% by weight.

12. The method of claim 10, wherein the step of cleaving the cumene hydroperoxide is performed at a temperature of 55 to 65° C.

13. The method of claim 12, further comprising the step of adding phenol to or removing acetone from the cleavage mass formed in step (a) to attain an acetone:phenol mole ratio of 1:20 to 1:10.

14. The method of claim 13, wherein the acetone:phenol mole ratio attained is 1:13.

15. The method according to claim 12, wherein step (b) is performed at a temperature of 40 to 100° C.

16. The method of claim 15, further comprising the step of adding phenol to or removing acetone from the cleavage mass formed in step (a) to attain an acetone:phenol mole ratio of 1:20 to 1:10.

17. The method of claim 16, wherein the acetone:phenol mole ratio attained is 1:13.

18. The method of claim 2, wherein the catalyst is sulfated zirconia.

19. The method of claim 18, wherein the step of cleaving the cumene hydroperoxide is performed at a temperature of 55 to 65° C.

20. The method of claim 18, further comprising the step of adding phenol to or removing acetone from the cleavage mass formed in step (a) to attain an acetone:phenol mole ratio of 1:20 to 1:10.

21. The method of claim 20, wherein the acetone:phenol mole ratio attained is 1:13.

22. The method according to claim 18, wherein step (b) is performed at a temperature of 40 to 100° C.

23. The method of claim 22, further comprising the step of adding phenol to or removing acetone from the cleavage mass formed in step (a) to attain an acetone:phenol mole ratio of 1:20 to 1:10.

24. The method of claim 23, wherein the acetone:phenol mole ratio attained is 1:13.

25. The method of claim 18, wherein the cation exchange catalyst comprises pyridyl ethyl mercaptan.

26. The method of claim 25, wherein the pyridyl ethyl mercaptan is loaded on the cation exchange resin in an amount of 20 to 70% by weight.

27. The method of claim 25, wherein the pyridyl ethyl mercaptan is loaded on the cation exchange resin in an amount of 40% by weight.

28. The method of claim 26, wherein the step of cleaving the cumene hydroperoxide is performed at a temperature of 55 to 65° C.

29. The method of claim 28, further comprising the step of adding phenol to or removing acetone from the cleavage mass formed in step (a) to attain an acetone:phenol mole ratio of 1:20 to 1:10.

30. The method of claim 29, wherein the acetone:phenol mole ratio attained is 1:13.

31. The method according to claim 28, wherein step (b) is performed at a temperature of 40 to 100° C.

32. The method of claim 31, further comprising the step of adding phenol to or removing acetone from the cleavage mass formed in step (a) to attain an acetone:phenol mole ratio of 1:20 to 1:10.

33. The method of claim 32, wherein the acetone:phenol mole ratio attained is 1:13.

34. The method of claim 1, wherein the catalyst is sulphated zirconia.

* * * * *

UNITED STATES PATENT AND TRADEMARK OFFICE
CERTIFICATE OF CORRECTION

PATENT NO. : 7,154,010 B2  Page 1 of 1
APPLICATION NO. : 10/250107
DATED : December 26, 2006
INVENTOR(S) : Kumbhar et al.

It is certified that error appears in the above-identified patent and that said Letters Patent is hereby corrected as shown below:

In the claims:

Col. 8, line 7 should read: --The method according to claim 19, wherein step (b) is--.

Signed and Sealed this

Twentieth Day of February, 2007

JON W. DUDAS
*Director of the United States Patent and Trademark Office*